US011744602B2

(12) United States Patent
Vetter et al.

(10) Patent No.: US 11,744,602 B2
(45) Date of Patent: Sep. 5, 2023

(54) ADVANCED MINIMALLY INVASIVE MULTI-FUNCTIONAL ROBOTIC SURGICAL DEVICES AND METHODS

(71) Applicant: TransMed7, LLC, Portola Valley, CA (US)

(72) Inventors: Eugene H Vetter, Portola Valley, CA (US); James W Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 281 days.

(21) Appl. No.: 15/433,115

(22) Filed: Feb. 15, 2017

(65) Prior Publication Data
US 2022/0117617 A1  Apr. 21, 2022

(51) Int. Cl.
*A61B 17/29* (2006.01)
*A61B 17/3201* (2006.01)
(Continued)

(52) U.S. Cl.
CPC .......... *A61B 17/29* (2013.01); *A61B 17/3201* (2013.01); *A61B 2017/00345* (2013.01);
(Continued)

(58) Field of Classification Search
CPC .......... A61B 17/30; A61B 2017/00398; A61B 2017/2938; A61B 17/29; A61B 17/3201;
(Continued)

(56) References Cited

U.S. PATENT DOCUMENTS

| 3,664,346 A | * | 5/1972 | Dunn | A61B 17/3201 81/424.5 |
| 4,763,669 A | * | 8/1988 | Jaeger | A61B 10/0291 606/174 |

(Continued)

FOREIGN PATENT DOCUMENTS

WO   2013056190 A1   4/2013

OTHER PUBLICATIONS

EPO Examination Report dated Aug. 11, 2016 in EP Appln 12839250.3.

(Continued)

*Primary Examiner* — Timothy J Neal
*Assistant Examiner* — Mitchell Brian Hoag
(74) *Attorney, Agent, or Firm* — YOUNG LAW FIRM, P.C.

(57) ABSTRACT

Minimally invasive, multi-functional robotic surgical tool devices for use as lavaging, material aspiration or delivery surgical forceps, scissors or clamp or other device, consisting of a monolithic work element and open central lumen with various functional tips. Such devices may in use follow a central lumen of another device or over a wire in a longitudinal direction upon introduction to a body. Flush and vacuum transport mechanisms, imaging mechanisms or energy source mechanisms may be incorporated. Inner and outer sheaths which may be co-axially disposed relative to a work element may be configured to actuate a beak or beaks and provisions for simultaneous beak closing under rotation may be incorporated.

4 Claims, 6 Drawing Sheets

(51) Int. Cl.
*A61B 17/00* (2006.01)
*A61B 17/30* (2006.01)

(52) U.S. Cl.
CPC ............ *A61B 2017/00353* (2013.01); *A61B 2017/00398* (2013.01); *A61B 2017/2902* (2013.01); *A61B 2017/2938* (2013.01); *A61B 2017/2939* (2013.01); *A61B 2017/305* (2013.01)

(58) Field of Classification Search
CPC .... A61B 2017/2902; A61B 2017/2939; A61B 2017/00345; A61B 2017/00353; A61B 2017/305
See application file for complete search history.

(56) References Cited

U.S. PATENT DOCUMENTS

| | | | |
|---|---|---|---|
| 5,203,785 A * | 4/1993 | Slater | A61B 17/29 606/174 |
| 5,373,854 A | 12/1994 | Kolozsi | |
| 5,827,305 A * | 10/1998 | Gordon | A61B 10/0266 606/159 |
| 6,030,409 A * | 2/2000 | Lang | A61B 17/320016 606/205 |
| 6,086,543 A | 7/2000 | Anderson | |
| 6,322,522 B1 | 11/2001 | Zimmon | |
| 8,118,755 B2 | 2/2012 | Hibner | |
| 8,133,237 B2 | 3/2012 | Oostman, Jr. et al. | |
| 8,568,410 B2 | 10/2013 | Vakharia | |
| 8,579,897 B2 | 11/2013 | Vakharia | |
| 8,603,135 B2 | 12/2013 | Mueller | |
| 8,696,671 B2 | 4/2014 | Solsberg et al. | |
| 2002/0169459 A1* | 11/2002 | Porat | A61B 17/122 606/120 |
| 2005/0267529 A1* | 12/2005 | Crockett | A61B 17/0643 606/215 |
| 2009/0062792 A1* | 3/2009 | Vakharia | A61B 18/1492 606/45 |
| 2010/0121153 A1 | 5/2010 | To | |
| 2011/0208236 A1* | 8/2011 | Ward | A61B 17/282 606/205 |
| 2012/0209140 A1 | 8/2012 | Ryan | |
| 2012/0330351 A1* | 12/2012 | Friedman | A61B 17/122 606/205 |
| 2013/0096459 A1 | 4/2013 | Vetter | |
| 2013/0317291 A1* | 11/2013 | Yamamoto | A61B 17/0487 606/147 |
| 2014/0142602 A1 | 5/2014 | Polo | |
| 2015/0112226 A1* | 4/2015 | Vetter | A61B 10/0266 600/567 |
| 2019/0374242 A1* | 12/2019 | Avigal | A61B 17/3201 |

OTHER PUBLICATIONS

USPTO Notice of Allowance dated Jan. 18, 2017 in U.S. Appl. No. 14/052,724.
USPTO Office Action dated Mar. 17, 2017 in U.S. Appl. No. 13/853,719.
USPTO Office Action dated Apr. 19, 2017 in U.S. Appl. No. 14/599,481.
USPTO Office Action dated Apr. 19, 2017 in U.S. Appl. No. 14/050,771.
USPTO Office Action dated May 22, 2017 in U.S. Appl. No. 14/491,348.
EPO Extended European Search Report dated Jun. 28, 2017 in EPO Appln. 14804925.7.
USPTO Notice of Allowance dated Jul. 5, 2017 in U.S. Appl. No. 13/853,806.
EPO Extended European Search Report dated Jun. 17, 2017 in EPO Appln. 14794839.2.

* cited by examiner

ADVANCED MINIMALLY INVASIVE MULTI-FUNCTIONAL ROBOTIC SURGICAL DEVICES AND METHODS

BACKGROUND

Embodiments relate to medical devices and methods. More particularly, embodiments relate to hand-held or stage mounted, including robotic arm manipulation, aspiration, material delivery and lavage, remote sensing, multi-functional surgical tool devices and corresponding methods for minimally invasive robotic or manual micro or macro surgical applications and manufacturing thereof. Embodiments further relate to improvements over currently used robotic tool systems, specifically in providing minimally invasive and more widely capable and reliable surgical devices and methods.

SUMMARY

Embodiments are drawn to medical devices and methods that may be used for surgical procedures. According to one embodiment, for example, a surgical tool device according to one embodiment may be configured as a tubular forceps device to remove liquids, solids, semi-solids and single or multiple material samples during an insertion through the skin (percutaneous procedure) or any orifice into any area of the body, as well as for cauterizing blood vessels. Embodiments may comprise structures and functionality for different phases of a multi-phase imaging, sensing and material delivery and removal surgical procedure or percutaneous procedure, which may be performed by hand or by attachment of the present device to an imaging stage or robotic arm, for example. Embodiments may also comprise devices configured for insertion through a lumen of another compatible excisional or surgical device as well as for introducing another compatible excisional or surgical device through the central lumen of one of the devices described herein. Embodiments may be configured to deliver surgical instruments of suitable compatibility to a targeted area of the body. Embodiments of a device, along with associated related subcomponents described herein, may be configured to retrieve solid, contiguous and/or fragmented materials as well as liquid and semi-solid materials for analysis, diagnosis or treatment. Such embodiments may also be configured to provide, in a single all-in-one instrument, improvements in functionality and performance relative to present devices and methods, such as surgical forceps, delivery and aspiration needles, scissors of various configurations, hemostatic clamps, staplers, clip appliers and combinations of clamps and clip appliers and severing devices, as well as aspiration systems, lavaging systems or imaging systems, for example. Embodiments may combine mechanical severing and sealing mechanisms with energized or energy enhanced capabilities that may include, for example, coagulation and severing functionalities. One or more energy sources may be provided (and/or combined with one another) including, for example, radiofrequency, ultrasonic and laser energy as well as simple cryogenic and thermal energy delivery, which may be delivered, for example, to the distal end and/or distal edges of a device according to embodiments. Embodiments may utilize distal edges to focus and concentrate energy delivery to enhance a biologic effect thereof, which may also be combined with delivery of certain photoactive agents or other chemical biologically active agents to achieve hemostasis, anti-organism effects and anti-inflammatory and pain-mitigating outcomes. Embodiments may comprise feedback loops to identify successful endpoints of desired effects and may include visual or other confirmation of endpoints. Although some embodiments may find particular utility in surgical intervention procedures, other embodiments may also find utility in, for instance, ex-vivo laboratory and other medical procedures or industrial applications, and are not to be limited, therefore, to the exemplary and illustrative surgical applications described, shown and claimed herein. Embodiments and elements thereof may be deployed in interventional surgical procedures, and may include a variety of features, designed to include and accomplish the equivalent functions of separate delivery devices to deliver medications, dyes, implants, other diagnostic or therapeutic medical materials, various forms of energy, and devices such as other interventional devices performing functions listed above as well as guiding elements including catheters and various types of guiding and interventional wires, imaging catheters and wires, contrast media, oxygenation elements, sensing instruments, radiation delivery elements, protective and shielding devices and others. Embodiments may also include a variety of features for, including but not limited to, tissue expansion, stent placement, expansion or retrieval, or placement or retrieval of other prosthetic or implantable devices during an interventional procedure. Embodiments may be configured to be portable, disposable or reusable and may be, for example, electrically/electronically-, mechanically-, hydraulically-, pneumatically- and/or manually-, powered, controlled and operated.

One embodiment, therefore, is a surgical forceps device, comprising: a single-piece articulated work element consisting of material cut from a single open-ended tube of material, the single-piece articulated work element defining an open hollow lumen centered on a longitudinal axis and comprising a proximal end, a distal end and a body portion therebetween. The distal end may define at least one tendon, at least one living hinge and at least one articulated beak configured to selectively assume configurations between fully open and fully closed to at least one of grasp tissue or an object. The proximal end may define a work element actuation element coupled at least to the at least one tendon, the single-piece articulated work element being configured such that movement, in a direction parallel to the longitudinal axis, of one portion of the work element actuation element relative to another portion of the work element actuation element selectively pushes and pulls on the at least one tendon, causes the at least one living hinge to flex and selectively moves the at least one beak to configurations between the open and closed configurations. An outer tube may be disposed at least partially over the work element.

The surgical forceps device may comprise a first articulated beak and a second articulated beak. An automated mechanical device may be coupled to the work element actuation element. Alternatively, a manually-driven mechanical device coupled to the work element actuation element.

Another embodiment is a surgical scissors device, comprising: a single-piece articulated work element consisting of material cut from a single open-ended tube of material, the single-piece articulated work element defining an open hollow lumen centered on a longitudinal axis and comprising a proximal end, a distal end and a body portion therebetween. The distal end may comprise a first articulated scissors element comprising at least one first tendon and at least one first living hinge, and a second articulated scissors element comprising at least one second tendon and at least one second living hinge. The first and second articulated scissors elements may be configured to selectively assume configurations between open and closed configurations. The proximal end may define a work element actuation element that is coupled at least to the at least one first and second tendons and that is configured such that movement, in a direction parallel to the longitudinal axis, of one portion of the work element actuation element relative to another portion of the work element actuation element selectively pushes and pulls on the at least one first and second tendons, causes the first and second living hinges to flex and selectively moves the first and second articulated scissors elements between the open and closed configurations to cut tissue (and any selected configuration between the fully open and the fully closed configurations). An outer tube may be disposed at least partially over the work element.

An automated mechanical device may be coupled to the work element actuation element. Alternatively, a manually-driven mechanical device may be coupled to the work element actuation element.

One embodiment is a surgical method of grasping tissue or an object, comprising providing an outer tube and a single-piece articulated work element disposed at least partially within the outer tube, the single-piece articulated work element consisting of material cut from a single open-ended tube of material and comprising an open hollow lumen centered on a longitudinal axis, a proximal end, a distal end and a body portion therebetween, the distal end defining at least one articulated beak, the proximal end defining a work element actuation element comprising a first portion and a second portion. At least the distal end may be inserted into a target area in tissue, a cavity or a biological conduit. The first portion of the work element actuation element may then be moved relative to the second portion of the work element actuation element, in a first direction parallel to the longitudinal axis, to at least partially open the at least one articulated beak within the target area. The first portion of the work element actuation element may then be moved relative to the second portion of the work element actuation element, in a second direction parallel to the longitudinal axis, to at least partially close the at least one articulated beak and grasp tissue or an object within the target area. At least the distal end of the forceps device may then be retracted from the target area, along with the tissue or object grasped by the work element.

Providing may be performed with the at least one beak comprising a first articulated beak and a second articulated beak and wherein the moving steps move both the first and second articulated beaks between open and closed configurations. An automated mechanical device may be coupled to the work element actuation element. Alternatively, a manual mechanical device may be coupled to the work element actuation element. The method may further comprise delivering a fluid, semi-solids and/or solids to the target area through the open hollow lumen. Providing may be performed with the distal end defining at least one tendon and at least one living hinge. Moving the first portion of the work element actuation element relative to the second portion of the work element actuation element in the first direction may be configured to push on the at least one tendon and flex the at least one living hinge one way; and moving the first portion of the work element actuation element relative to the second portion of the work element actuation element in the second direction may be configured to pull on the at least one tendon and flex the at least one living hinge an other way.

According to another embodiment, a method of surgically cutting tissue may comprise providing an outer tube and a single-piece articulated work element disposed at least partially within the outer tube, the single-piece articulated work element consisting of material cut from a single open-ended tube of material and comprising an open hollow lumen centered on a longitudinal axis, a proximal end, a distal end and a body portion therebetween, the distal end comprising a first articulated scissors element and a second articulated scissors element configured to selectively assume configurations between fully open and fully closed. At least the distal end may then be inserted into a target area in tissue, a cavity or a biological conduit. The first portion of the work element actuation element may be moved relative to the second portion of the work element actuation element, in a first direction parallel to the longitudinal axis, to at least partially open the first and second articulated scissors elements within the target area. The first portion of the work element actuation element may then be moved relative to the second portion of the work element actuation element, in a second direction parallel to the longitudinal axis, to at least partially close the first and second articulated scissors elements to cut tissue within the target area.

An automated mechanical device may be coupled to the work element actuation element. Alternatively, a manual mechanical device may be coupled to the work element actuation element. Fluids, semi-solids and/or solids may be delivered to the target area through the open hollow lumen. Providing may be performed with each of the first and second articulated scissors elements comprising at least one tendon and at least one living hinge, and moving the first portion of the work element actuation element relative to the second portion of the work element actuation element in the first direction may be configured to push on the at least one tendons and flex the at least one living hinges one way. Moving the first portion of the work element actuation element relative to the second portion of the work element actuation element in the second direction may be configured to pull on the at least one tendons and flex the at least one living hinges an other way.

DETAILED DESCRIPTION

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, an advanced multi-functional surgical tool device (shown at reference 10 in the Figures) may be configured for material or tissue removal, manipulation or excision and may be configured to manipulate or remove materials in the fields of, for example, cardiovascular, orthopedic, thoracic, muscular system, reproductive or urogenital systems, endocrine system or neurologic intervention. Embodiments are well suited to instances in which a minimally invasive, multi-use, precise forceps system is desired that is configured for removal of hard, soft or liquid tissue materials or foreign bodies. The present device may, according to different implementations, comprise a range of work element dimensions ranging from, for example, approximately 0.0065" to 0.249" diameter (⅓ French to 19 French); 4 gauge to 32 gauge or any other appropriate dimensions, both larger and smaller, depending on applications and field of use requirements. According to embodiments, a surgical tool device may comprise a generally rigid or semi-flexible or flexible tubular structure, which may be at least partially disposed within a coaxially-disposed outer tube or tubes. A distally located work element, according to one embodiment, may comprise one or more grasping, manipulating and/or cutting elements. In one embodiment, one or more of the cutting elements may be configured as a beak with smooth or serrated edges or other features designed to grasp, hold, slice or manipulate materials. One or more of such beaks may be fixed or articulable, sharpened or unsharpened, smooth or serrated at their tips or along their side axes. Various combinations thereof may be devised, with different combinations of such features and elements being interchangeable, according to embodiments.

According to embodiments, a generally tubular shaped surgical tool device 10 may comprise an open central lumen that may incorporate structures configured to facilitate and enable a number of intra-operative combinations of adjunctive procedures that may be associated with such forceps use, such as the delivery of lavage fluids and other medical materials or radioactive materials to the target tissue surgical site; aspiration features designed to remove liquids and semi-solids including foreign materials; and/or delivery features for analgesics, antibiotics, markers, implant materials and other materials. According to further embodiments, such a device 10 may incorporate any of a number of imaging, sensing or interventional components, such as miniature cameras, ultra-sonic sensors, super-magnets, Geiger counters, cauterization wires or RF or plasma energy cutting elements, impedance measuring sensors, electrolyte and other chemical or optical sensors, light sources such as visible spectrum, ultra-violet or infra-red sources and associated image capturing systems and other subsystem elements that may be introduced through the open central lumen of a device and also, for instance, be embedded in an outer sheath over the generally tubular work element. In one embodiment, the outer sheath may comprise or be made of, for example, polyimide (Kapton®), shrink wrap or other suitable material. According to one embodiment, the surgical tool device 10 may be advanced to a target area within tissue over a wire, such as a pre-placed guidewire, for example. According to one embodiment, the surgical tool device configured as a forceps device 10 may be advanced to or near the target area within a cannula or other interventional coring or surgical forceps device. According to further embodiments, a device 10 may be configured to be sterilizable and reusable and may feature replaceable tubular forceps of different sizes and combinations of features removably coupled to a common handle. According to further embodiments, a device 10 may be configured as a surgical scissors or any combination of surgical forceps, clamp, needle and/or scissors for remote immobilization and cutting applications by modification of the beak shape(s) or by, for instance, laser welding additional structures to the beaks. It is to be understood that references throughout this description to surgical forceps may also be applicable to other embodiments, in which a device 10 may be configured for primary use as a clamp, scissors, cauterizing device or other device described herein. According to embodiments, device 10 may be flexible, rigid or a combination of such characteristics over its axial length, and may be configured to work outside of or internal to various vascular, lymphatic or other tubular structures to meet interventional goals and procedures. According to embodiments, such a device 10 may be used to expand tissue at a target location in order to allow other interventional tools to access and work on an adjacent tissue. According to further embodiments, a device 10 may be configured to place or retrieve prosthetic materials, such as stents, scaffolds, implants, embolic, radio-active sources or other materials.

According to one embodiment, as an illustrative example, a surgical forceps device 10 may be advanced into the body percutaneously to reach a target tissue site for the retrieval or removal of a foreign body such as a shard of metal, brachytherapy seeds, breast marker or any other piece of tissue or object whose removal is desired. Along the path through the tissue to the target tissue site, analgesics may be eluted through the open central lumen of the device to the distal end of the device, which may be in its open or closed position, as desired by the interventionist, to control pain associated with the interventional procedure. Once the distal tip of the work element has been advanced and has grasped the foreign body, lavage fluid or other fluids such as, for example, medications may be introduced distally through the open central lumen of device 10 for purposes of, for example, disinfecting or expanding the surrounding tissue and releasing the foreign body for subsequent withdrawal from the patient's body. The lavage fluid or other fluid may be aspirated and replaced intra-operatively with, for example, antibiotic agents and/or other beneficial material, which may also serve to coat the pathway in reverse as the foreign body is withdrawn. Sensing agents located at the distal tip or introduced through the central lumen of the device may provide image or other guidance technology to and from the target site, and other elements and features incorporated in device 10, according to various embodiments, may also function as cauterization elements to control bleeding at the site, either prior to, during or subsequent to foreign body immobilization and retrieval procedures. Device 10 may be used for any purpose associated with common uses for forceps, tweezers, needles, clamps or scissors, with the addition of pre-, intra- or post-operative structures, as described herein. According to one embodiment, such a device 10 may be used, for example, for retrieving markers, embolic beads, radioactive beads, bone shards or other materials with real time precise imaging at the tip of the device during an interventional procedure.

Beak (distal working end) actuation for the purposes of cycling between closed-state (for penetration and material grasping, for example) and wide open state (for manipulation or capturing materials, for example) while twisting, rotating or remaining steady in relation to a target may, according to one embodiment, be accomplished with a push-pull mechanism that originates in a driving assembly far proximal to the beak structures themselves, as long as the connection between a proximal driver and the movable structures, including the movement of living backbone hinge elements relative to living hinge/tendon/keystone elements of the beaks, is comprised of structures that can transmit small movements precisely, relying on column strength structural integrity combined with relatively inelastic tension structures to transmit these direct, linear forces over the length of the tubular elements between the beaks and driver mechanism.

Herein, beaks may refer to that portion of a work element whose primary functions may comprise manipulation or grasping to hold, sever or remove material, or to deliver material or perform other functions. Beaks may be fixed, articulable, sharpened or unsharpened, may have serrations along the distal edges and may have various other features and shapes according to various embodiments. Beaks may comprise longitudinal living hinge elements such that the beaks may be expanded "out of round" to a more flattened shape, or alternatively a more tubular shape than when at rest, and may also allow the beaks of the forceps device to expand to a configuration greater than the circumference of the beaks at rest to allow grasping larger structures. The driving assembly or assemblies (hereafter, collectively "driving assembly" for ease of reference) of the beaks may be controllable at the proximal handle end of the device (e.g., outside the body). The driving assembly may also comprise variable control as needed and may also include the ability to halt the motion of the work element at any desired procedural phase, with rearward (proximal) translation for purposes of delivering removed or excised materials such as pieces of tissue or foreign material. According to one embodiment, vacuum (along with fluid management) may aspirate or deliver liquids or materials to the interventional site. Such vacuum and flush systems may be augmented with an internal helix or helices or Archimedes screw-type augers or variants thereof, to aid in the management and proximally-directed delivery of tissues, foreign bodies, blood and/or other fluids. The driving assembly may also be configured for the delivery of electrical, mechanical, radiant, ultrasonic, electromagnetic, electron beam and simple magnetic, among other, energies distally to a work element area, whereby conversion or re-conversion to another energy form (the addition or removal of heat, for example) may be made in the work area. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

It is to be noted that, herein, the phrase "helical element" and the terms "helix" or "helices" are intended to encompass a broad spectrum of structures. Indeed, the structures shown herein are but possible implementations of a helical element, helix or helices. According to other embodiments, "helical element", "helix" or "helices" and equivalent expressions may be implemented as tubes having one or more slot-shaped openings or fenestrations along at least a portion of the length thereof. Such fenestrations may be substantially parallel to the longitudinal axis of a tube or may be disposed, for example, in a spiral configuration. The fenestrations may be continuous along at least a portion of the length of a tube or may be discontinuous, such as to result in a plurality of such parallel or spirally wound fenestrations. The fenestrations may be very wide such that the resultant structure resembles a spring, or more narrow, such that the resulting structure more closely resembles a tube having narrow, slot-shaped openings therein. The continuous or discontinuous fenestrations may be caused to assume other configurations along at least a portion of the tubes in which they are formed. For example, the fenestrations may be caused to form a zigzag pattern such as "NNNN . . . ", "/VVVVV" or "VVVV . . . " or a cross-shaped pattern, such as "XXXXX". Significantly, the terms "helical element," "helix," or "helices" should be understood to cover a spectrum of structures, from a spring-like structure to tubes having selected slot-shaped openings, with such tubes exhibiting rigid or flexible portions along their lengths. Tubes or tubular elements, as described herein may, according to embodiments, incorporate helical elements to their structures.

As used throughout this disclosure, work elements may comprise one or more tubes, and the terms "inner" and "outer" tubes or sheaths may be used with reference to a single work element, or in reference to two or more co-axially located work elements, each of which may comprise one or more tubes to enable their specific function. A coaxially-disposed outer tube, according to one embodiment, may also comprise one or more coatings. According to one embodiment, a tube may comprise a stainless steel hypodermic tubing ("hypo tube") or may comprise mild steel elements at various locations for various functions. Such a stainless hypo tube, according to one embodiment and method, may be provided with (e.g., laser) cuts to define a monolithic distal assembly that defines one or more beaks, a living hinge that attaches the beak(s) to the generally tubular body of the device or that homogeneously spans between the beak(s) and the generally tubular body of the device. According to one embodiment and method, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. In this manner, the work element, including the one or more beaks, may be formed of tube material left over after a number of cuts have been made and tube material selectively removed from the hypo tube. In this manner, an articulable beak or beaks may be formed simply by selective removal of material from a hollow, open-ended tube. According to one embodiment, portions of the tube may be rigid. According to another embodiment and method, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element, according to the intended application or environment of use (soft tissue, hard tissue, cartilage or bone, for example). This device may be used by itself or may be used in conjunction with or inside another surgical device with an open central lumen, through which it may introduced to attack a target tissue site. Similar elements, structures, features and functionality contained in this disclosure are disclosed in co-pending and commonly assigned U.S. patent application Ser. No. 13/973,898 entitled "SOFT TISSUE CORING BIOPSY DEVICES AND METHODS"; U.S. patent application Ser. No. 14/050, 771 entitled "SOFT TISSUE CORING BIOPSY DEVICES AND METHODS"; U.S. patent application Ser. No. 62/052,070 entitled "SOFT TISSUE BIOPSY OR EXCISIONAL DEVICES AND METHODS"; U.S. patent application Ser. No. 62/052,591 entitled "IN-SITU MATERIAL DELIVERY DEVICES AND METHODS"; U.S. patent application No. 61/876,977 entitled "TISSUE CORING BIOPSY DEVICES AND METHODS"; and U.S. patent application Ser. No. 14/864,146 entitled "EXCISIONAL DEVICES AND METHODS", the entire disclosures of which are hereby incorporated herein in their entirety.

Figure 1:
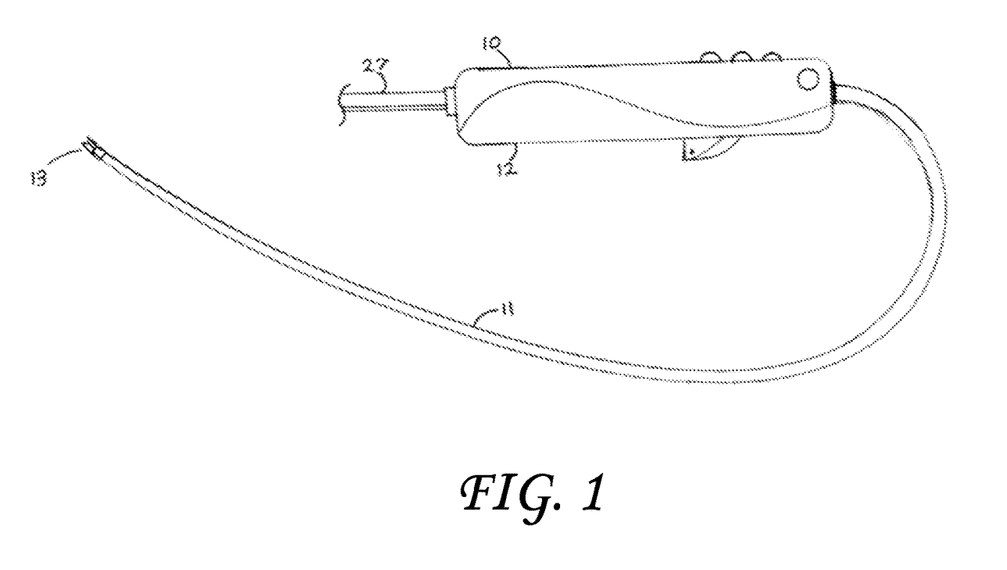
FIG. 1 is a perspective side view of a surgical device, according to one embodiment.

FIG. 1 shows a surgical forceps device 10 according to embodiments. As shown, the forceps device 10 may comprise a neck element 11 comprising a tubular open central lumen configured for aspiration, lavage, material delivery, imaging and/or sensing. The neck element 11 may be of any suitable dimensions to grasp, manipulate or retrieve materials consistent with use of a surgical forceps device sufficient to provide the desired clinical surgical, diagnostic or therapeutic result. The neck element 11 may be, for example, about 6-40 inches in length and of any appropriate outside diameter. It is to be understood, however, that the foregoing dimensions and any dimensions referred to herein are exemplary in nature only and are not limiting factors. Those of skill in this art will recognize that other dimensions and/or configurations may be implemented, depending upon the application, and that a tubular forceps assembly and its subparts could be of any length or outside diameter.

One embodiment of the surgical forceps device 10, as shown in the figures, may be implemented as a hand-held device comprising an ergonomically comfortable and secure handle 12 at its proximal end from which neck 11 comprising a tubular open central lumen assembly extends so that the device 10 may be easily directed with one hand while the other hand is free to hold a guiding probe such as an ultrasound transducer. However, it is to be understood that embodiments may readily be configured to fit onto any number of guiding devices such as, but not limited to, a stereotactic, computed tomography (C.T.), or 3-D Tomography imaging stage or other guidance modality such as Magnetic Resonance Imaging (MRI). As shown, one embodiment of the device 10 may comprise one or more blunt or sharp, smooth or serrated edge rotatable work elements 13 (herein, alternatively and collectively referred to as "work element", "beak", "beak assembly" or "beak element" or "beak elements") projecting forward distally from the distal free end of the neck element for the purpose of forward penetration, morcellation, excision, grasping, twisting and/or other manipulation, singly or in combination, of a target tissue or foreign body in a simple point and capture procedure. It is to be understood that the "tubular" description of a tubular open central lumen assembly may be a generally tube-shaped element of any cross-section shape and size, of any length. The components of neck 11 comprising the tubular open central lumen assembly 11 also transfer collected tissues and fluids back proximally along the internal length of an inner lumen of a tubular open central lumen assembly to a handle 12 and thus to any suitable containment device, which may be attached to the handle 12. The handle 12 may also contain and/or be coupled to (internal or external) mechanical components (not shown) for vacuum-assisted fluid evacuation at element 27 as well as the delivery of materials such as, for example, a variety of flushes, medications, tracer materials and/or implantable marker elements (not shown). The distal tubular open central lumen assembly 11, according to one embodiment, may be configured with the smallest possible caliber (e.g., diameter), with a range of, for example, about 16 gauge or 0.065 inches in diameter to about 1 inch or more diameter, while enabling the diameter of its open forceps beaks to be sufficiently large as to be clinically useful.

According to methods and embodiments, the neck 11 comprising the tubular open central lumen assembly may also comprise or be constructed of flexible materials and/or of a sufficient length to reach target sites that are distant from the surface of the skin without the need for a surgical procedure, to enable the distal end (that end thereof that is furthest from a handle 12) of the device 10 to reach the targeted site. Embodiments of the present device 10 may be used by right and/or left handed persons and in multiple positions and orientations so that in areas of limited access the present device may still be easily positioned for ideal orientation to perform an interventional procedure under real-time or other image guidance (not shown). The entire device may be configured to be disposable or may be configured to be reusable in whole or in part.

Embodiments of the present device 10 may be electrically powered by one or more batteries and/or external power sources (e.g., a 12V car battery, for example) through a simple electrical coupling to connect to an external power supply conveniently placed, for example, in a handle or proximal end of the present device. The forceps beaks at the distal tip may, for example, be manually operated or by solenoid or other mechanism. The entire device may also be internally or externally manually powered, mechanically powered or be powered by means such as compressed air, gas or pressurized fluid. Powering the device entirely mechanically may be advantageous in areas in which the electric grid is absent, unavailable, or unreliable.

Figure 2:
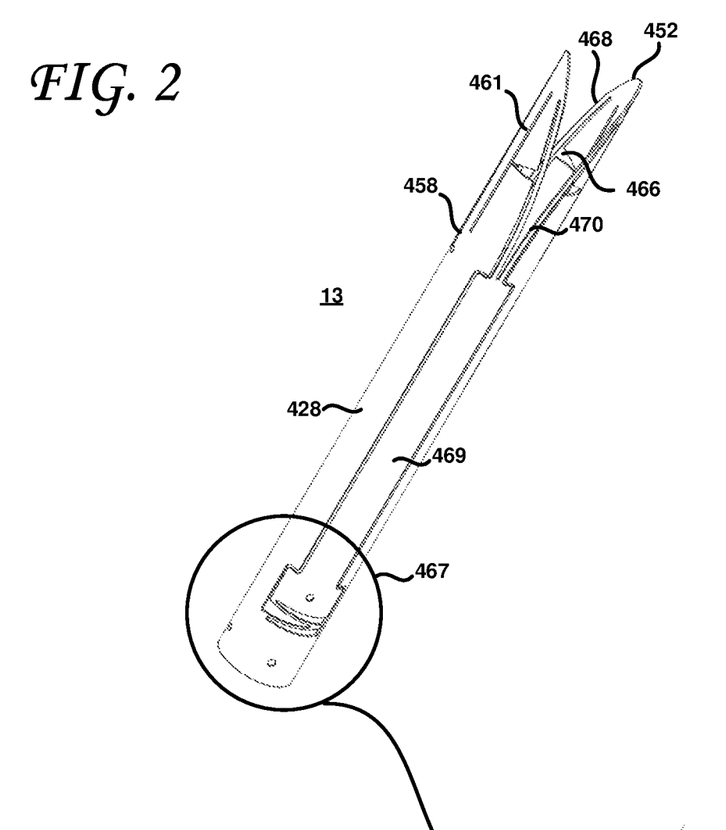
FIG. 2 shows a monolithic beak assembly of a multi-use surgical device according to one embodiment.
Figure 3:
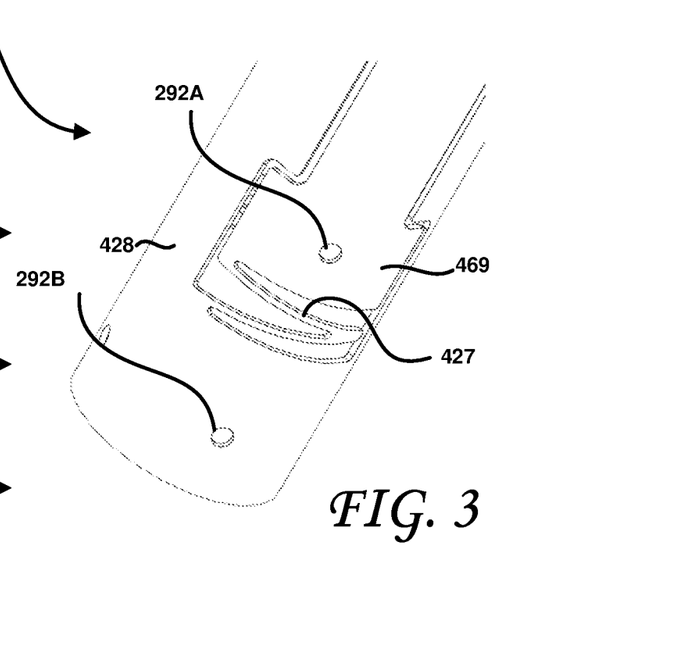
FIG. 3 shows a detail of a monolithic forceps beak assembly of a surgical device, according to one embodiment.

FIGS. 2 and 3 show details of components of a work element, according to one embodiment. Attention is drawn to the proximal end of the work element 13, best shown in FIG. 3. Therein, a body portion 428 of the work element 13 may be mechanically coupled to a tendon actuating element 469 at or near the proximal end of a work element. Note that the tendon actuating element 469 is already coupled to a body portion 428 through tendons 468, 470, toward the distal end of a work element 13. That is, an entire work element 13 may be formed of a single homogeneous piece of material—such as from a single hollow tube that is (for example) laser-cut to form all of the structures shown in FIGS. 2 and 3. Two beaks are shown in FIG. 2, with each beak having serrated edges for use as forceps, according to one embodiment. According to other embodiments, the edges of the beaks may be sharp for use as scissors or blunt for use as clamps. According to still further embodiments, additional features such as scissors blades or clamp faces may be attached to opposing beak structures and crimped, glued and/or laser-welded in place. It is to be understood that such a work element 13 may comprise multiple beaks or a single beak that acts against a non-moveable part, such as a fixed trough-shaped distal portion or against a fixed, opposing beak that is part of a work element 13 itself.

FIGS. 2 and 3 show the distal, working end 13 of a device according to one embodiment. The working end 13 may be coupled to a hand-held device as shown in FIG. 1, a stereotactic device or to a device for robotically-assisted surgical device. According to one embodiment, as shown in FIGS. 2 and 3, the working end 13, shown here in a two-beak implementation, may comprise, at a proximal end thereof, a tendon actuating element 469 that may be mechanically coupled to the proximal portion of a body portion 428. Such mechanical coupling may be configured to maintain the tendon actuating element 469 centered on the cutout in a body portion formed to accommodate the tendon actuating element 469 and/or to provide additional biasing force in the distal direction, as well as to aid in manufacturing. One embodiment comprises a resilient member 427 having one end thereof coupled to a tendon actuating element 469 and another end thereof coupled to a proximal portion of the work element 13. Such a resilient member 427 may be configured to bias the beak or beaks of work element 13 in the open configuration, such that a sufficiently great proximally-directed force applied to a tendon actuating element 469 tends to close the beak or beaks. Conversely, release of such proximally-directed force causes the resilient member 427 to release the energy stored during the extension thereof and return to its un-extended state, thereby exerting a distally-directed force on a tendon actuating member 469, which causes the beak or beaks to return to its or their default open configuration, according to embodiments. According to other embodiments, the beaks may be configured to be biased in the closed configuration. According to further embodiments, the base of the work element 13 (proximal to locating hole 292B in FIG. 3) may be prolonged proximally to the handle 12 of the device, and may be rigid along its length or flexible. It is significant, both for structural integrity, strength as well as ease of manufacturing, that all of the structures shown in FIGS. 2 and 3 may be formed from a single open-ended tube of material, from which tube material may be removed (through laser-cutting, in one embodiment), to leave the structures shown in FIGS. 2 and 3. According to one embodiment, no structures of the working end extend beyond the outer diameter of the tube from which the working end 13 was formed. Similarly, no structures extend within the inner diameter of the tube from which the working end 13 was formed. When the beak(s) are open, in plan view, the working end 13 looks just like the tube from which it was cut. Significantly, the structures enabling the articulation of the beak or beaks of the working end 13; namely, the tendons 468, 470, the living hinge 461, the tendon actuating member 469 and the resilient member (among other structures) are configured to have the same profile as the tube from which the working end was fashioned, without protruding in or out. This makes the working end 13 have the smallest possible cross section for a given diameter inner lumen, with all the attendant benefits for the patient. For example, due to its low profile, the device may be easily guided immediately next to delicate structures to grasp and retrieve tissue samples, foreign objects, implants and the like, according to one embodiment. According to other embodiments, structures for functional purposes such as grasping, cutting or other purposes may be formed of a single, laser cut tube, and then the tips may be further formed by, for example, crimping, laser welding, sharpening, or other method, and in which case the distal tip of the device may partially occlude the central lumen when in open or closed positions, according to methods.

Also shown in FIG. 3, attachment hole 292A and fixture hole 292B may be provided on a body portion 428 and on the tendon actuating element 469, respectively. Such attachment/fixture holes 292 may, according to one embodiment, indicate the location of, for example, spot welds or fixture pin locating holes, as detailed below. Either an automated mechanical device (including a robotic assembly, for example) 302 or a manual mechanical assembly 304 (such as shown in FIG. 1) may be coupled to the work element actuation element 469, to move tendon actuating member 469 relative to the body portion 428 to selectively push on or pull the tendons 468, 470 to selectively open and at least partially close the beak or beaks. An energy source 306 may be coupled to the device to energize the beak or beaks according to a selected treatment modality, as discussed above.

Figures 4, 5:
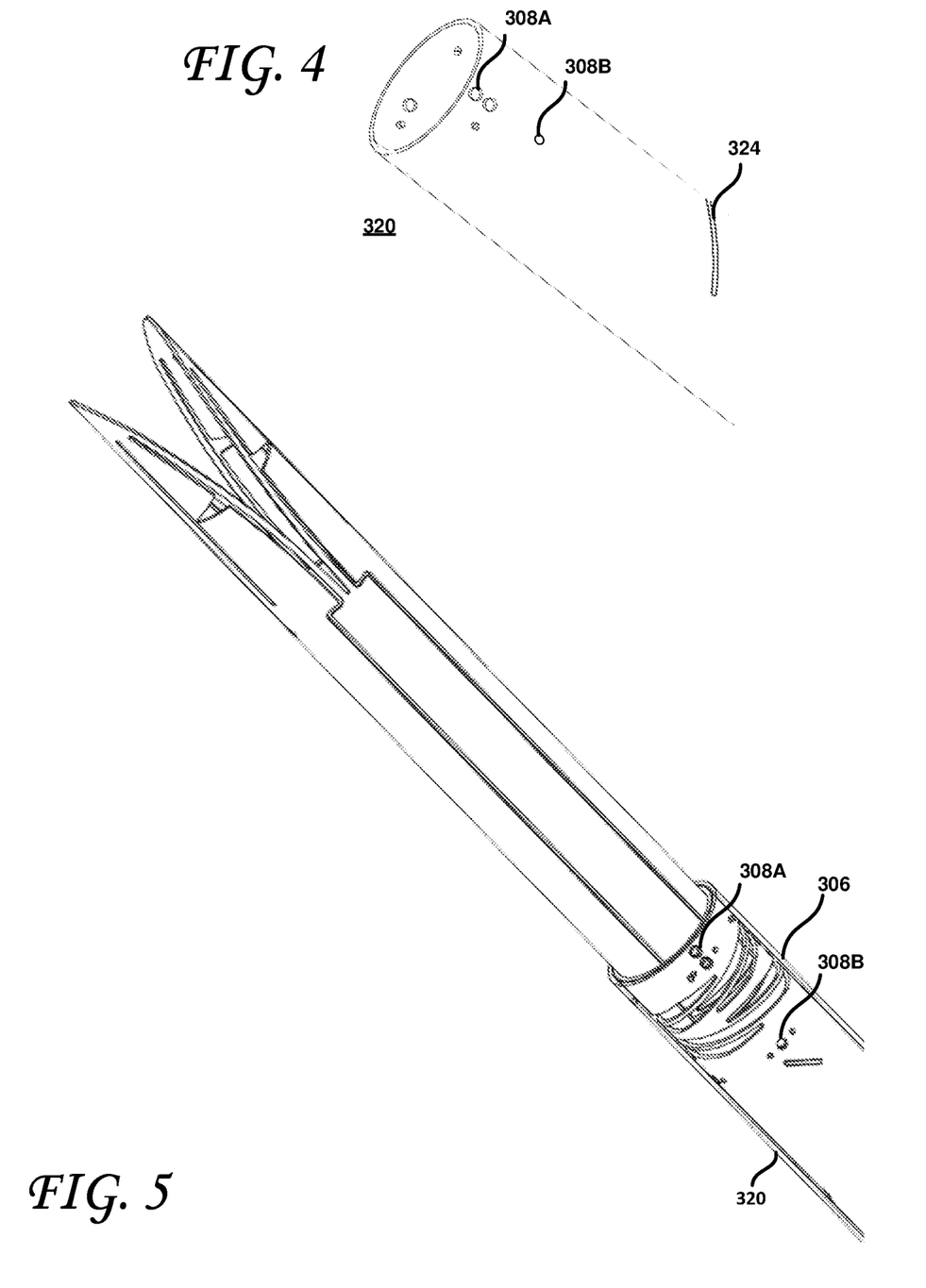
FIG. 4 illustrates the distal end of an outer tube of a device, according to one embodiment.
FIG. 5 illustrates details of an assembled work element and outer tube of a surgical device, according to one embodiment.

FIG. 4 shows a distal portion of an outer, coaxial tube that may be configured to fit over and attach to the work element 13 of FIG. 2 above, according to one embodiment. An outer tube 320, as shown in FIG. 4 may comprise a number of fenestrations or slots 324 that run through the wall of the tube 320, from an outer surface to an interior lumen thereof. The distal portion of outer tube 320 may be configured to fit over and attach to the actuation element 469 of monolithic beak assembly (work element) 13 of FIGS. 2 and 3. During assembly of the present surgical forceps device and as shown in FIG. 5, attachment/fixture holes 308A and 308B of outer tube 320 may be lined up with attachment/fixture holes 292A and 292B, respectively, of the monolithic beak assembly 13. An assembly aligning pin (not shown) may be inserted into fixture holes 292B and 308B to hold the assembly in place and a spot weld may be applied to holes 292A and 308A, followed by removal of the assembly aligning pin. Other attachment method/means may be implemented, as those of skill in this art may recognize. As shown in FIG. 5, additional (e.g., laser) cuts may be defined in the distal end of outer tube 320, which may act as spring tension elements when the beak(s) is/are closed, which may be advantageous when applying a constant closing force to the forceps beaks of work element 13. In this manner, axial movement between the tubular shaped work element 13 and outer tube 320 will thus serve to actuate the beaks of the work element 13. Outer tube 320, which may be flexible along its length, may thus be attached to a monolithic beak assembly 13 at attachment points 292A and 308A. Although not shown in these figures, corresponding attachment points may be provided on the hidden side of the device. As also shown in FIG. 5, the distal portion of the outer tube 320 may define a resilient or spring portion, as shown at reference numeral 306 as described above.

Figures 6A, 6B:
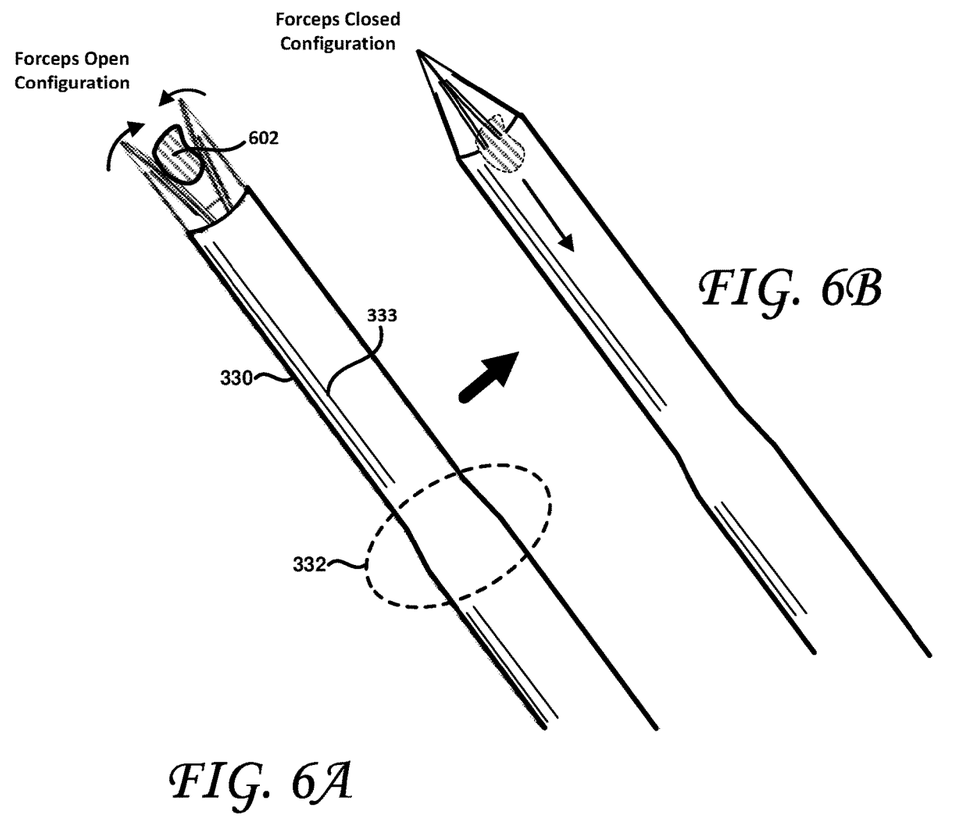
FIG. 6A illustrates structure and functionality of a surgical forceps device, according to one embodiment.
FIG. 6B illustrates further structure and functionality of a forceps device, according to one embodiment.

FIG. 6A shows one embodiment of a surgical tool, in this instance, a forceps device, in a still further state of assembly and in a first, open, configuration. FIG. 6B shows the surgical forceps device of FIG. 6A in a second, closed, configuration. In FIGS. 6A and 6B, an outer sheath 330 has been fitted over an assembly comprising a monolithic beak assembly 13 and outer tube 320, according to one embodiment. According to one embodiment, the outer sheath 330 may comprise polyimide or may comprise or be formed of stainless steel among other suitable materials. The outer sheath 330 may be configured to be rotating, non-rotating, or at least differentially-rotating with respect to the assembly comprising a monolithic beak assembly 13 and outer tube 320 and may further be configured to be removable. The outer sheath 330 may extend distally to beaks of a monolithic beak assembly, may expose a greater proportion of a monolithic beak assembly 13 or may cover a significant portion of beaks, which may be controlled during use, according to embodiments. The beak or beaks may have different shapes and may include scoop-shaped or castellated configurations. Such structures may extend beyond the distal end of the outer tube 320 by a predetermined or selectively variable amount.

According to one embodiment, the outer sheath 330 may be dimensioned so as to allow an annular space to exist between the inner wall of an outer sheath 330 and the combined outer surfaces of the outer tube 320 and distal portion of a monolithic beak assembly 13. This annular space may allow for flush to be introduced at selected stages in the procedure. The outer sheath 330 may contain elements such as embedded wires 333 (e.g., conductive traces in a polyimide sheath, for example) or other features corresponding to imaging devices, energy delivery devices or sensing devices (not shown) as described previously. Such elements 333 may also be simple channels as opposed to embedded wires for use in exchanging sensing elements at the tip of the device as may be desired by the operator, according to embodiments and methods. Additionally, according to one embodiment, an expanded area of the outer sheath 330, as shown in the area 332, may act on the distal end of the outer tube 32, and thus if the work element 13 is forced distally, the work element forceps beaks may be actuated closed (as shown in FIG. 6B) or partially closed, as may be desired, according to methods.

As shown in FIG. 6A, according to one method, the forceps device may be guided immediately proximal to a piece of tissue or object 602 to be retrieved. In approaching the piece of tissue or object 602, the forceps device may be in either the open beak configuration or the closed beak configuration. If in the open beak configuration, the forceps device may be rotated, facilitating the tissue penetration. As it advances through the tissue to the target area where the piece of tissue or object 602 is located, it may collect a tissue core within its internal lumen. This core may be severed from surrounding tissue by closing the beak or beaks. Alternatively, the approach to the target area where the piece of tissue or object 602 is located may be in a closed beak configuration, with the forceps device following a natural body passageway such as vasculature or may be caused to dissect tissue it encounters as the distal tip is advanced. Either way, the forceps device may capture (and not necessarily fully encapsulate) the piece of tissue or object 602 within its beaks as shown in FIG. 6A and close its beaks to capture the piece of tissue or object 602 within the interior lumen thereof, as shown in FIG. 6B. The piece of tissue or object 602 is shown in dashed lines in FIG. 6B, to suggest its capture within the forceps device. Thereafter, structures within the interior lumen of the forceps device and/or flush and/or vacuum may facilitate the transport thereof in the proximal direction. Alternatively, the captured piece of tissue or object 602 may be grasped by partially-closed beaks and the entire device retracted, dragging the captured piece of tissue or object 602 along with it, for retrieval outside of the body. In such a scenario, the beaks may only partially close over the piece of tissue or object 602, with a portion thereof protruding distally from the distal-most tips of the beaks.

Figure 7A:
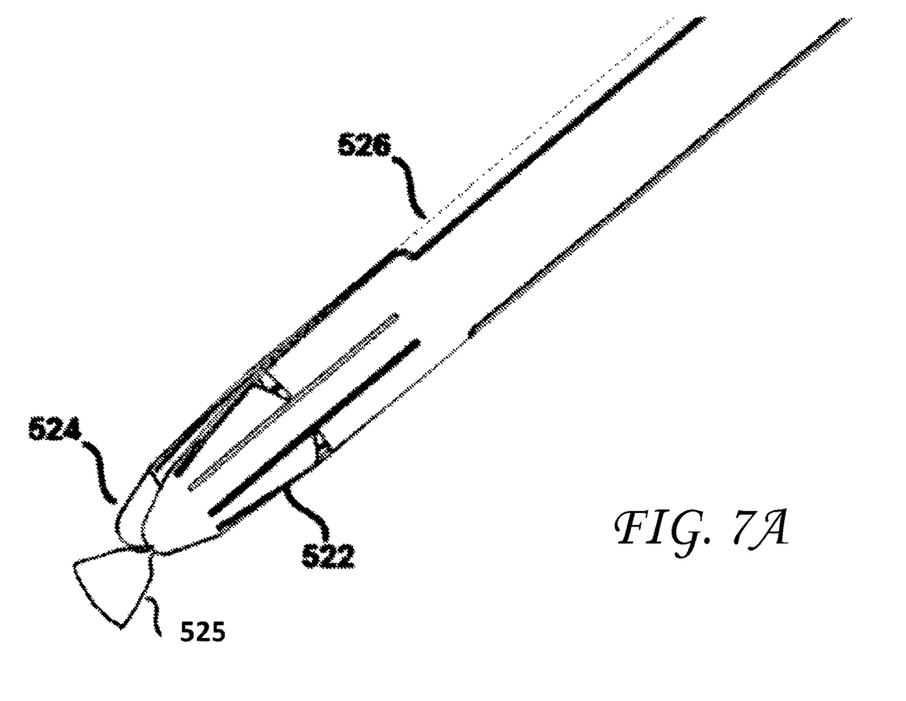
FIG. 7A illustrates further structure and functionality of a multi-use surgical device, according to one embodiment.

FIG. 7A illustrates one embodiment and method of forming a surgical forceps or clamp. In this illustration, the work element of such a device is cut from a single tube by, for instance, laser cutting, to selectively remove material from the tube. The body of the tube, in this embodiment, comprises a tendon actuation element 526, such as described previously herein, tendons 522 and distal tips 524 and 525. In this embodiment, a method of forming the forceps or clamp includes a laser cut extension 525 of the general beak shape on both beaks. Such an extension may be a simple mirror image of the more proximal section, and with a small tab connecting the extension to the beak tip. According to one method, once the laser cut pattern is achieved, as illustrated by beak extension 525, the extension may simply be flattened laterally and folded back, still connected to its tab, inside its respective beak, and may be laser welded at its edges as shown with beak 524. In such an embodiment, a flat surface is thus fabricated at the inner surface of each beak end, suitable for use as either a clamp or forceps, for example. Since the shape of the beaks may be configured completely occlude when closed, the opposing flat surfaces will also occlude, according to one embodiment. According to one embodiment for making a forceps, the beak edges may be serrated. According to another method, the beaks may not have an extension, and the flat surfaces on the inner tips of the beaks may be built up by laser welding and grinding their opposite surfaces flat. Other methods of manufacturing for such surgical tools will occur to one skilled in the art, and are considered to be within the scope of this specification.

Figure 7B:
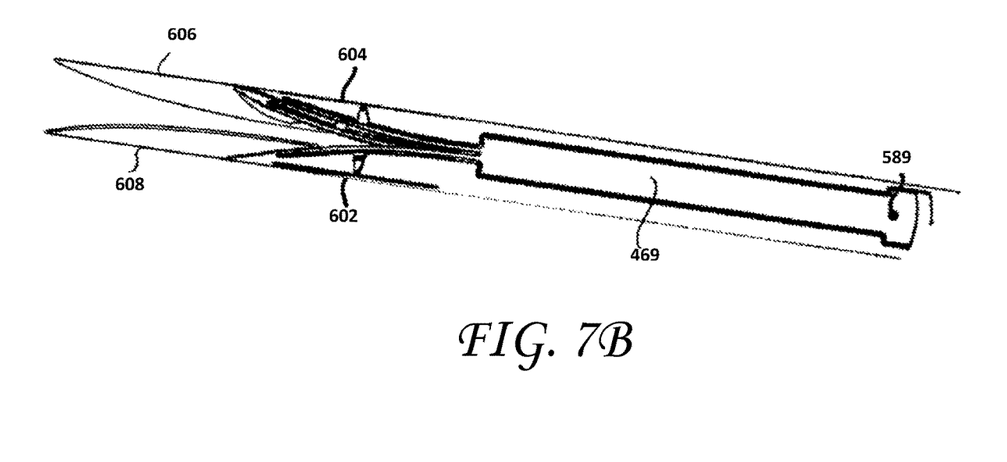
FIG. 7B illustrates further structure and functionality of a surgical scissors device, according to one embodiment.

FIG. 7B illustrates a method of forming a scissors tip for a surgical device, according to one embodiment. In this figure, an extension similar to element 606 is laser cut with the beaks 604 and 602 in a tube, such as a hypotube, to form a monolithic work element. Blade element 606 represents such an extension in its generally tubular form once laser cut, and element 608 represents a blade element in its final form, in which the blade extension is longitudinally flattened by crimping and laser welded along its joined inner edges to form an articulated scissors element extending forward from the tip of beak 602. Once flattened and laser welded, its inner edge may be sharpened. The same procedure may be used on blade element 606, and once completed, the two articulated scissors elements may be aligned and tempered as necessary to provide opposed cutting surfaces, according to one embodiment.

Figure 7C:
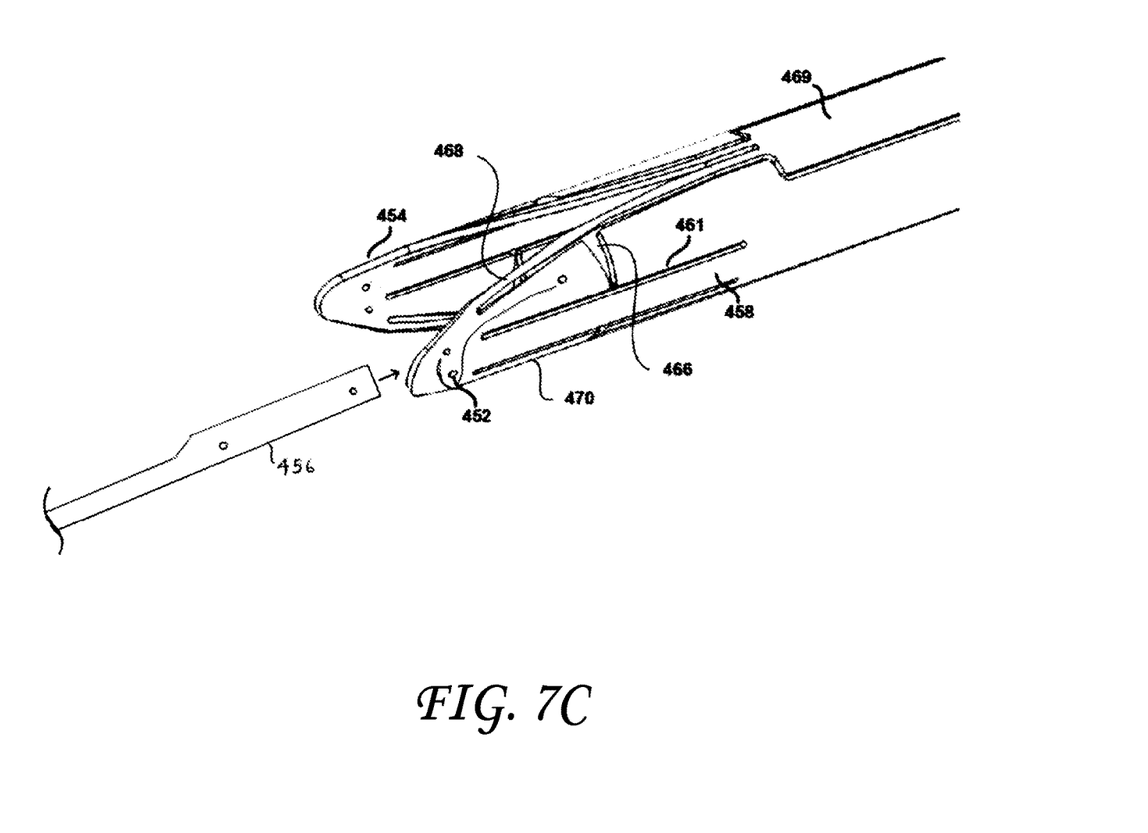
FIG. 7C illustrates further structure and functionality of a multi-use surgical device, according to one embodiment.

FIG. 7C illustrates one embodiment of forming and attaching any of a number of generic or commonly used surgical device working tips to a monolithic work element such as described above. In this illustration, an extension 456, which may terminate in any of a number of surgical tool configurations, such as an extended trocar, needle, forceps, scissors, clamp, or other tool (not shown), may be attached to a monolithic work element by aligning laser weld holes 452 with the corresponding weld hole locations of tool tip element 456. According to one method, tool tip element 456 is slid inside one of the beaks of the monolithic work element, and then the tips of the beaks are crimped and flattened longitudinally at the weld holes 452 to clamp the tool tip element 456 to the beaks as an extension of the beaks. Once clamped, a simple laser welding at each of the two holes corresponding to those found in tool tip element 456 will serve to firmly attach the tool tip element to the beak. A similar tool tip element 456 corresponding to that to be fixed to the opposite beak 454 may then be located and welded to the opposite beak (not shown in this illustration.)

The described embodiments may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a work element 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safekeeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A surgical device, comprising:
a single-piece articulated work element consisting of material cut from a single open-ended tube of material, the single-piece articulated work element defining an open hollow lumen centered on a longitudinal axis and comprising a proximal end, a distal end and a body portion therebetween, wherein:
the distal end defines a first articulated beak and a second articulated beak, each of the first and second articulated beaks comprising at least one tendon and at least one living hinge, the first and second articulated beaks being configured to selectively assume open and closed configurations and
the proximal end defines a work element actuation element coupled at least to the at least one tendon, the single-piece articulated work element being configured such that movement, in a direction parallel to the longitudinal axis, of the work element actuation element relative to another portion of the single-piece articulated work element selectively pushes and pulls on the at least one tendon, causes the at least one living hinge to flex and selectively moves the at least one beak to configurations between the open and closed configurations;
a first scissor element attached to a distal end of the first articulated beak and a second scissor element attached to a distal end of the second articulated beak, such that the first and second scissor elements open and close as the first and second articulated beaks open and close, respectively, and such that the first and second scissor elements operate as scissors to cut tissue, and
an outer tube disposed at least partially over the work element.

2. The surgical device of claim 1, wherein the at least one beak comprises a first articulated beak and a second articulated and wherein a first extension is attached to the first articulated beak and a second extension is attached to the second articulated beak.

3. The surgical device of claim 1, wherein the scissors is configured to be operated manually.

4. The surgical device of claim 1, wherein the scissors is configured to be operated automatically.

* * * * *